United States Patent
Chung et al.

(10) Patent No.: US 7,994,148 B2
(45) Date of Patent: Aug. 9, 2011

(54) TRANSMEMBRANE DELIVERY PEPTIDE AND BIO-MATERIAL COMPRISING THE SAME

(75) Inventors: Ji-Hyung Chung, Seoul (KR); Yang-Soo Jang, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 224 days.

(21) Appl. No.: 12/375,913

(22) PCT Filed: Aug. 2, 2007

(86) PCT No.: PCT/KR2007/003734
§ 371 (c)(1),
(2), (4) Date: Jan. 30, 2009

(87) PCT Pub. No.: WO2008/016276
PCT Pub. Date: Feb. 7, 2008

(65) Prior Publication Data
US 2009/0269842 A1     Oct. 29, 2009

(30) Foreign Application Priority Data
Aug. 3, 2006 (KR) .................. 10-2006-0073238

(51) Int. Cl.
*A61K 31/70* (2006.01)
*A01N 63/00* (2006.01)
*C12N 15/74* (2006.01)
*C07K 7/00* (2006.01)
*C07H 21/04* (2006.01)

(52) U.S. Cl. ...... 514/44; 424/93.2; 424/93.21; 435/325; 530/300; 536/23.1

(58) Field of Classification Search .................. None
See application file for complete search history.

(56) References Cited

U.S. PATENT DOCUMENTS
5,652,122 A   7/1997   Frankel et al.
5,998,206 A   12/1999  Cowsert

FOREIGN PATENT DOCUMENTS
KR   10-2005-0029879   3/2005

OTHER PUBLICATIONS

International Search Report and Written Opinion dated Nov. 8, 2007, in Application No. PCT/KR2007/003734.
Iida, A. et al., "Identification of 20 nevel SNPs in the guanine nucleotide binding protein alpha 12 gene locus." J. Hum. Genet. vol. 49(8) pp. 445-448, Jun. 18, 2004.

*Primary Examiner* — Q. Janice Li
(74) *Attorney, Agent, or Firm* — Holme Roberts & Owen LLP (57) ABSTRACT

The present invention relates to a transmembrane delivery peptide derived from human in which a target protein may be easily delivered into cells, and a recombinant vector comprising a nucleic acid coding the peptide. More specifically, the present invention relates to the transmembrane delivery peptide having an amino acid sequence described in SEQ ID No. 1 including 11 amino acids of specific sites in amino acid sequences of human G protein alpha 12, and a recombinant vector comprising a nucleic acid coding the same, a transformant prepared by introducing said recombinant vector, and the like. Since transmembrane delivery peptides of the present invention can be efficiently delivered into cells, they may be usefully used for the purposes of delivering various target materials, including proteins, nucleic acid, drugs and the like.

10 Claims, 7 Drawing Sheets

GNP-1 : 5'-GGCAGC<u>CATATG</u>GCGCGCGACGCGGAGCGCGAGGCCCGGAGGCGT <u>GGATCC</u>GAATTC-3'

GNP-2 : 3'-CCGTCG<u>GTATAC</u>CGCGCGCTGCGCCTCGCGCTCCGGGCCTCCGCA <u>CCTAGG</u>CTTAAG-5'

-Underlined sequences: NdeI, BamHI site
-Bold sequences: 33 base sequences coding 11 amino acid GNP-TDP

(A) Concentration 0    0.2    0.5    1.0    2.0    (uM)

(B) Time 0    0.2    0.5    1.0    2.0    (min)

EGFP treated group    GNP-EGFP treated group    (100 X)

SEQUENCE LISTING

<160> NUMBER OF SEQ ID NOS: 8

<210> SEQ ID NO 1
<211> LENGTH: 11
<212> TYPE: PRT
<213> ORGANISM: Artificial Sequence
<220> FEATURE:
<223> OTHER INFORMATION: Transmembrane Delivery Peptide from Human G
      protein alpha 12

-continued

```
<400> SEQUENCE: 1

Ala Arg Asp Ala Glu Arg Glu Ala Arg Arg
  1               5                  10

<210> SEQ ID NO 2
<211> LENGTH: 33
<212> TYPE: DNA
<213> ORGANISM: Artificial Sequence
<220> FEATURE:
<223> OTHER INFORMATION: Nucleotide Sequence Coding the Transmembrane
      Delivery Peptide

<400> SEQUENCE: 2
gcgcgcgacg cggagcgcga ggcccggagg cgt                                33

<210> SEQ ID NO 3
<211> LENGTH: 57
<212> TYPE: DNA
<213> ORGANISM: Artificial Sequence
<220> FEATURE:
<223> OTHER INFORMATION: Nucleotide Sequence Comprising the Sequence
      Represented by SEQ. ID. No. 2 (GNP-1)

<400> SEQUENCE: 3
ggcagccata tggcgcgcga cgcggagcgc gaggcccgga ggcgtggatc cgaattc      57

<210> SEQ ID NO 4
<211> LENGTH: 57
<212> TYPE: DNA
<213> ORGANISM: Artificial Sequence
<220> FEATURE:
<223> OTHER INFORMATION: Nucleotide Sequence Complementary to SEQ. ID.
      No. 3 (GNP-2)

<400> SEQUENCE: 4
gaattcggat ccacgcctcc gggcctcgcg ctccgcgtcg cgcgccatat ggctgcc      57

<210> SEQ ID NO 5
<211> LENGTH: 27
<212> TYPE: DNA
<213> ORGANISM: Artificial Sequence
<220> FEATURE:
<223> OTHER INFORMATION: Forward Primer for EGFP Gene

<400> SEQUENCE: 5
ccggtcgaat tcatggtgag caagggc                                       27

<210> SEQ ID NO 6
<211> LENGTH: 30
<212> TYPE: DNA
<213> ORGANISM: Artificial Sequence
<220> FEATURE:
<223> OTHER INFORMATION: Reverse Primer for EGFP Gene

<400> SEQUENCE: 6
gtcgcgctcg agttacttgt acagctcgtc                                    30

<210> SEQ ID NO 7
<211> LENGTH: 33
<212> TYPE: PRT
<213> ORGANISM: Artificial Sequence
<220> FEATURE:
<223> OTHER INFORMATION: Protein Transduction Domain of TAT Protein

<400> SEQUENCE: 7

Thr Tyr Arg Gly Leu Tyr Ala Arg Gly Leu Tyr Ser Leu Tyr Ser Ala
  1               5                  10                  15
```

-continued

```
Arg Gly Ala Arg Gly Gly Leu Asn Ala Arg Gly Ala Arg Gly Ala Arg
            20                  25                  30
Gly

<210> SEQ ID NO 8
<211> LENGTH: 20
<212> TYPE: DNA
<213> ORGANISM: Artificial Sequence
<220> FEATURE:
<223> OTHER INFORMATION: T7 Promoter Sequence

<400> SEQUENCE: 8
taatacgact cactataggg                                           20
```

TRANSMEMBRANE DELIVERY PEPTIDE AND BIO-MATERIAL COMPRISING THE SAME

CROSS-REFERENCE TO RELATED APPLICATIONS

The present application is a U.S. National Phase patent application under 35 U.S.C. §371 of International Application No. PCT/KR2007/003734, filed Aug. 2, 2007, which claims priority to South Korean Patent Application No. 10-2006-0073238, filed Aug. 3, 2006, both of which are expressly incorporated herein by reference.

TECHNICAL FIELD

The present invention relates to a transmembrane delivery peptide (abbreviated to "TDP," below). More specifically, the present invention relates to the transmembrane delivery peptide derived from human G protein (guanine nucleotide-binding protein), which may be usefully used for intracellular delivery of bio-functional materials such as proteins, nucleic acids, drugs, and the like.

BACKGROUND ART

It is noted that protein transduction domains, which are called PTDs, may be used in researches on intracellular action mechanisms of proteins or efficient technology for applying proteins in clinical therapeutic agents, with in the early 1990s, knowing that some of proteins can enter into cells by penetrating cell membrane in living cells (Derossi et al., 1994, *J. Biol. Chem.*, 269, 10444-10450). Particularly, such protein transduction domains may deliver materials such as nucleic acids or liposomes as well as macromolecules such as proteins into cells (Lewin et al., 2000, *Nature Biotech.*, 18, 410-414; Torchilin, 2002, *Cell. Mol. Biol. Lett.*, 7, 265-267).

Protein transduction domains known to date are peptides (TAT) derived from basic domains of HIV-1-derived TAT proteins, homeodomains (Antp) derived from Antennapedia of *Drosophila*, HSV-derived transcription factors (VP22) and synthetic lysine/arginine peptides, and the like (Wadia and Dowdy, 2003, *Curr. Protein Pept. Sci.*, 4, 97-104). It was shown that among them, the most studied TAT peptide consisted of a domain of a total 11 basic amino acid domain from 47$^{th}$ to 57$^{th}$ amino acids (YGRKKRRQRRR, SEQ ID No. 7) in amino acid sequences of the TAT protein, and said TAT peptide only was also delivered alone or in the form of fused with other proteins into cell membranes (Vives et al., 1997, *J. Biol. Chem.*, 272, 16010-16017). In addition, the TAT-PTD can deliver various proteins with a molecular weight in range of 10 kDa to 120 kDa, regardless of size, into cells (Fawell et al., 1994, *Proc. Natl. Acad. Sci. USA.*, 91, 664-668; Nagahara et al., 1998, *Nature Med.*, 4, 1449-1452). Moreover, it was identified that proteins fused with the TAT-PTD can be not only delivered into eukaryotic cells, but also have an inherent biological function of each protein in the cells and perform the function in the cells. The same result was reported even in an experiment using animal models such as a mouse (Asoh et al., 2002, *Proc. Natl. Acad. Sci. USA.*, 99, 17107-17112; Cao et al., 2002, *J. Neurosci.*, 22, 5423-5431).

To deliver proteins into cells by protein transduction domains is an independent mechanism, regardless of delivery methods previously known by receptors, transporters or endosomes, and it is assumed that their specific structural motifs or alignments by amino acids such as arginine or lysine affect on delivery ability of such protein transduction domains (Ho et al., 2001, *Cancer Res.*, 61, 474-477). In addition, while knowing that only arginine oligomers have ability to be effectively delivered into cells, in contrast with histidine, lysine and the like, among positive charged amino acids, it is known that only electric charges of amino acids do not affect on intracellular delivery ability (Wender et al., 2000, *Proc. Natl. Acad. Sci. USA.*, 97, 13003-13008). In case of intracellular delivery by HIV-1-derived TAT-PTD, the secondary structural motifs of amino acids such as α-helix play an important role, and it is reported that such α-helix structure maximizes substantially protein delivery efficiency (Ho et al., 2001, *Cancer Res.*, 61, 474-477).

As described in the above, protein delivery peptides that deliver target proteins having intracellular functions into cells or tissues are efficient methods for delivering proteins, nucleic acids or drugs. Besides the first found TAT-PTD, various protein transduction domains had been found or synthesized. However, all conventionally known protein transduction domains are peptides derived or synthesized from virus and the like, and thus may substantially cause problems such as immune responses on applying them in human. Therefore, it is very important to find novel protein transduction domains derived from human that can replace the protein transduction domains known to date.

The inventors of the present invention found that some of full length amino acid sequences of human G protein α-12 served as transmembrane delivery peptides. Then, recombinant vectors coding said peptides were prepared, to which recombinant genes of target proteins were inserted so as to fuse with target proteins, followed by expressing and purifying proteins in *Escherichia coli* strains. Then, the proteins were delivered into animal cells. They identified this fact by biological methods to accomplish the present invention.

DISCLOSURE

Technical Problem

An object of the present invention is to provide novel transmembrane delivery peptides derived from human capable of delivering target proteins into cells, nucleic acids coding said peptides, recombinant vectors including said nucleic acids fused with genes coding target proteins, and transformants prepared by introducing said recombinant vectors.

Technical Solution

To achieve the above object, the present invention provides a transmembrane delivery peptide having an amino acid sequence described in SEQ ID No. 1 derived from human G protein alpha 12.

The present invention also provides a nucleic acid coding said peptide.

The present invention also provides a recombinant vector comprising said nucleic acid.

The present invention also provides a recombinant vector that a gene coding a target protein is inserted into said recombinant vector.

The present invention also provides a transformant prepared by introducing said recombinant vector.

The present invention also provides a method for expressing and mass-producing a fused protein from a transformant prepared by introducing said recombinant vector.

Further, the present invention provides a method for introducing a target protein into cells by treating said recombinant vector in which a gene coding the target protein is inserted in a cell-containing culture medium or in vivo.

DESCRIPTION OF DRAWINGS

Lane M; protein marker,
Lane 1; sample before induction of IPTG,
Lane 2; sample 4 hours after induction of IPTG,
Lane 3; supernatant sample from cell debris,
Lane 4; sample from Ni-NTA column chromatography,
Lane 5; sample from Q-sepharose column chromatography,
Lane 6; sample from PD-10 desalting column

BEST MODE

The present invention is explained in detail below.

The present invention provides a transmembrane delivery peptide having an amino acid sequence described in SEQ ID No. 1 derived from human G protein alpha 12.

The present inventors have searched candidate sequences that have probably protein transduction domains in human genes, and found that among these sequences, a peptide consisting of 11 amino acid sequences from $29^{th}$ alanine to $39^{th}$ arginine in a total 381 amino acid sequences of G protein alpha 12 has a function to deliver fused proteins into cells. Since said peptide can effectively deliver target proteins into cells, it may be usefully used in delivering various proteins, nucleic acids and drugs into cells. The present inventors called said peptide "GNP-TDP (guanine nucleotide-binding protein transmembrane delivery peptide)."

The present invention also provides a nucleic acid coding said peptide.

The nucleic acid of the present invention includes all base sequences being capable of coding the transmembrane delivery peptide described in SEQ ID No. 1. Among these, it is preferred to have a base sequence described in SEQ ID No. 2.

The present invention also provides a recombinant vector comprising said nucleic acid.

The term "recombinant vector" herein is a vector that may express target proteins in suitable host cells, and means a genetic construct comprising necessary regulatory elements to be operable linked so as to express genetic inserts.

The vectors of the present invention include, but not limited to, plasmid vectors, cosmid vectors, bacteriophage vectors and virus vectors. Suitable expression vectors include signal sequences or leader sequences for membrane targeting or secretion as well as expression regulatory elements such as promoters, operators, start codons, stop codons, polyadenylated signals and enhancers, and may be variously prepared depending on purposes. Promoters in vectors may be constitutive or inducible. In addition, vectors include selective markers for selecting host cells comprising vectors, and in case of replicable vectors, they include an origin of replication.

Figure 2:
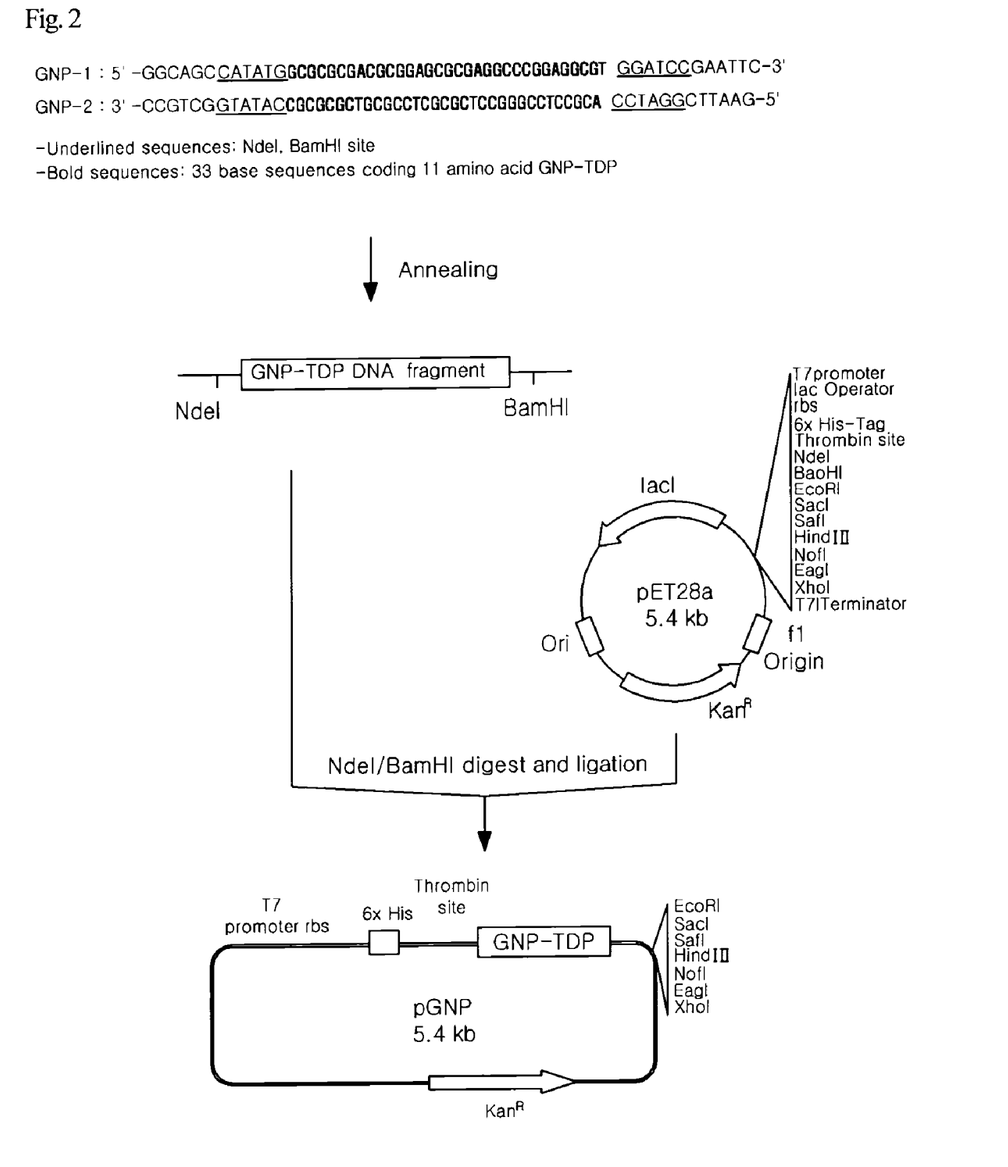
FIG. 2 is a pattern diagram showing a procedure for constructing a pGNP vector by inserting the fragment coding GNP-TDP into a pET28a vector.

Preferably, the recombinant vectors of the present invention may be prepared by inserting nucleic acids coding a peptide described in the SEQ ID No. 1 into general *Escherichia coli* expression vector. *Escherichia coli* expression vector used in preferred examples of the present invention is pET28a, but it is not necessarily limited to this. All generally usable *Escherichia coli* expression vector may be used without limitation. In preferred examples of the present invention, a recombinant vector, called "pGNP," was prepared by inserting a DNA fragment including a GNP-TDP base sequence described in SEQ ID No. 2, using pET28a, *Escherichia coli* expression vector (ref. FIG. 2).

The present invention also provides a recombinant vector that genes coding target proteins are inserted into said recombinant vector.

Figure 3:
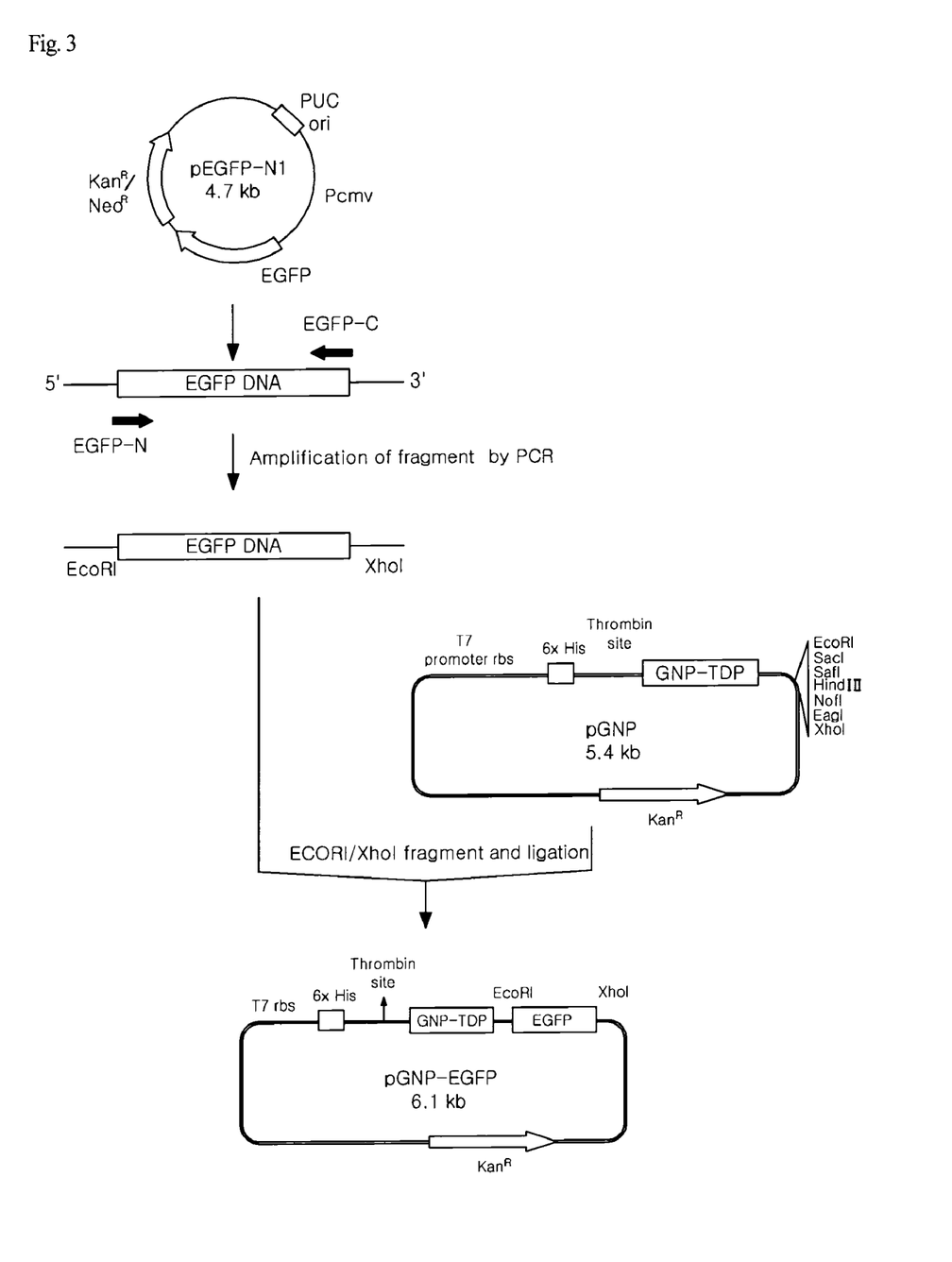
FIG. 3 is a pattern diagram showing a procedure for constructing a pGNP-EGFP vector by inserting DNA coding EGFP (enhanced green fluorescent protein) into a pGNP vector.

Target proteins are prepared in a form of fused proteins, using the recombinant vector. Then, to directly identify intracellular delivery efficiency, a recombinant vector in which EGFP genes are inserted into pGNP is prepared in preferred examples of the present invention, wherein this is called "pGNP-EGFP" (ref. FIG. 3). The target proteins above are not limited to specific proteins, for example, only EGFP used in the preferred examples of the present invention, and the like, but it is evident that all kinds of proteins may be used without limitation.

The present invention also provides a transformant prepared by introducing said recombinant vector.

Transformation may be carried out via methods being able to introduce nucleic acids into organisms, cells, tissues or organs, and may be performed by selecting suitable standard technology according to host cells, as known in this field. These methods are, but not limited to, electroporation, plasmogamy, calcium phosphate ($CaPO_4$) precipitation, calcium chloride ($CaCl_2$) precipitation, agitation using silicone carbide fiber, *Agrobacterium*-mediated transformation, PEG, dextran sulfate, lipofectamine, and the like.

Since expression level and modification of proteins vary depending on host cells, host cells that are most suitable for purposes should be selected and used. Host cells include, but not limited to, prokaryotic host cells such as *Escherichia coli*, *Bacillus subtilis*, *Streptomyces*, *Pseudomonas*, *Proteus mirabilis* or *Staphylococcus*. In addition, lower eukaryotic cells such as fungi (for example, *Aspergillus*), or yeasts (for example, *Pichia pastoris, Saccharomyces cerevisiae, Schizosaccharomyces, Neurospora crassa*), insect cells, plant cells, or cells derived from higher eukaryotes including mammals may be used as host cells.

Said transformants may be easily prepared by introducing said recombinant vectors into optional host cells. In preferred examples of the present invention, transformants were prepared by introducing said pGNP vector and a recombinant vector for expression pGNP-EGFP, wherein target protein of EGFP was inserted into said pGNP vector, into *Escherichia coli* strain DH5α.

In addition, the present invention provides a method for expressing target proteins fused with transmembrane delivery peptides using said transformed cells.

Figure 4:
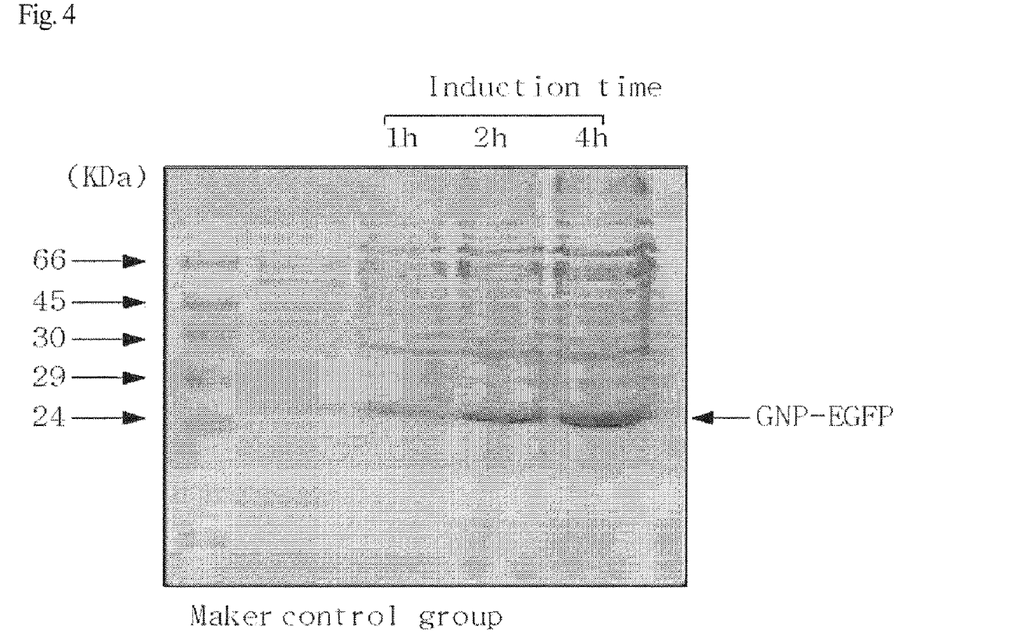
FIG. 4 is a photograph showing results that cell extracts, comprising the over-expressed GNP-EGFP recombinant proteins obtained by transforming a pGNP-EGFP plasmid into *Escherichia coli* strains, incubating and treating them with IPTG, and then sampling them by the hour, were subjected to electrophoresis in a SDS-polyacrylamide gel.
Figure 5:
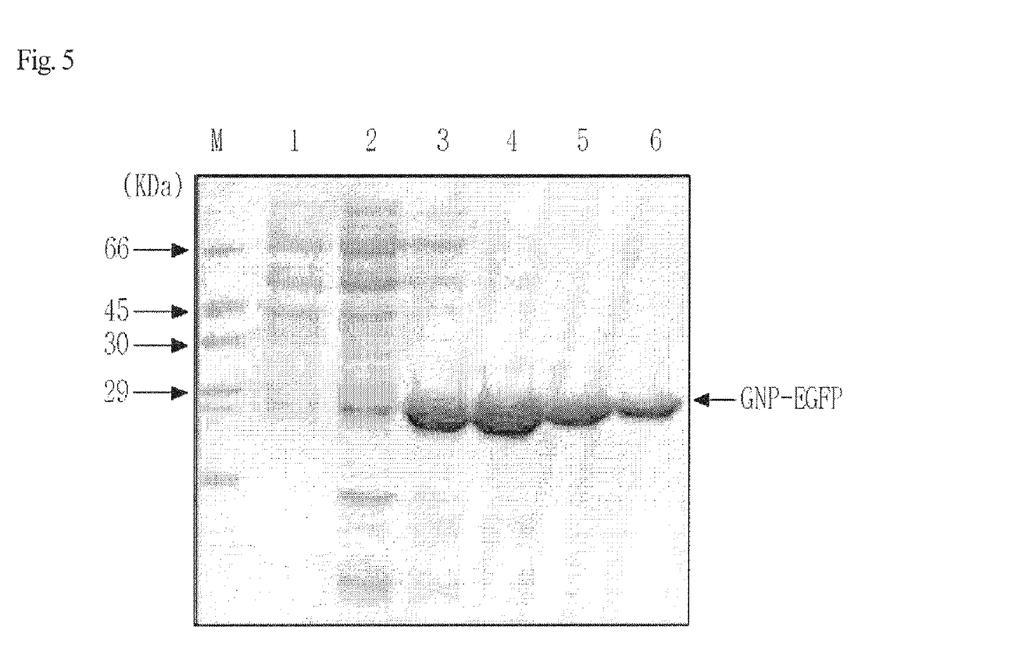
FIG. 5 is a photograph showing results that each sample obtained from purifying the GNP-EGFP recombinant proteins over-expressed in *Escherichia coli* strains through a Ni-NTA column chromatography and a Q-sepharose column chromatography was subjected to electrophoresis in a SDS-polyacrylamide gel.
Figure 7:
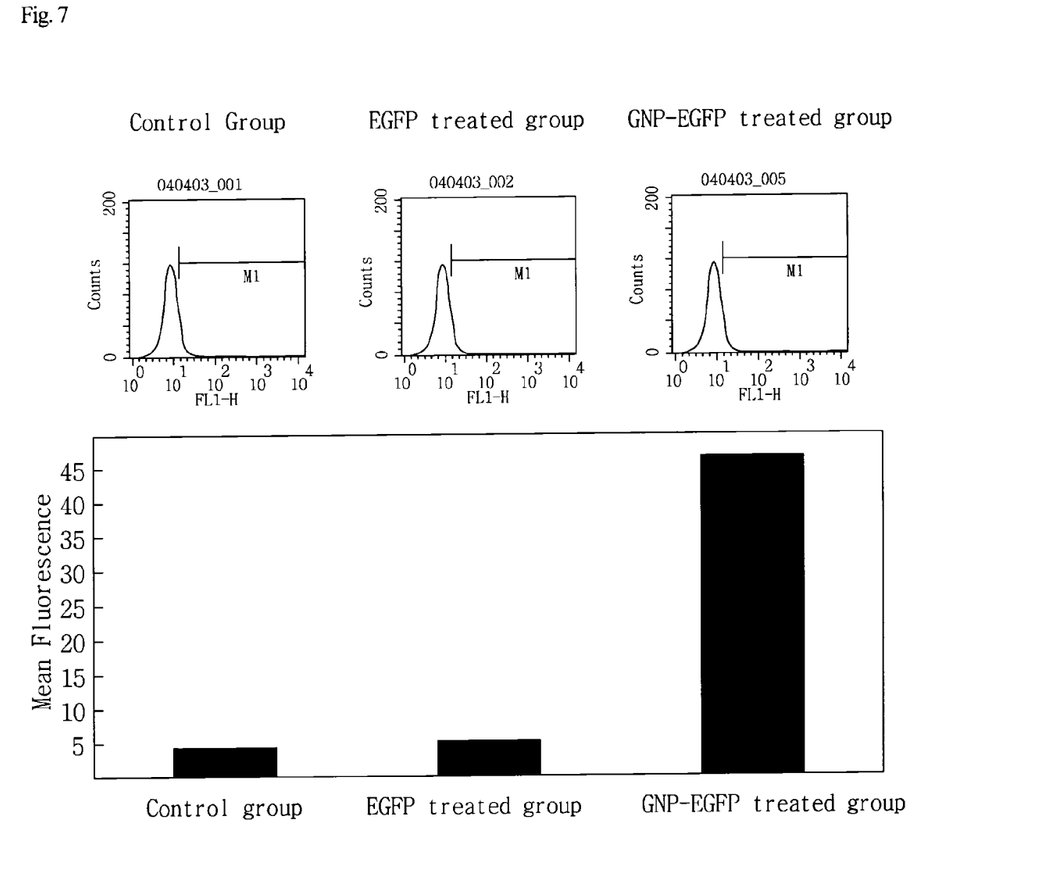
FIG. 7 is graphs showing results that the purified recombinant protein GNP-EGFP was treated in an animal cell line H9c2, and proteins delivered into cells were analyzed using a flow cytometer.
Figure 8:
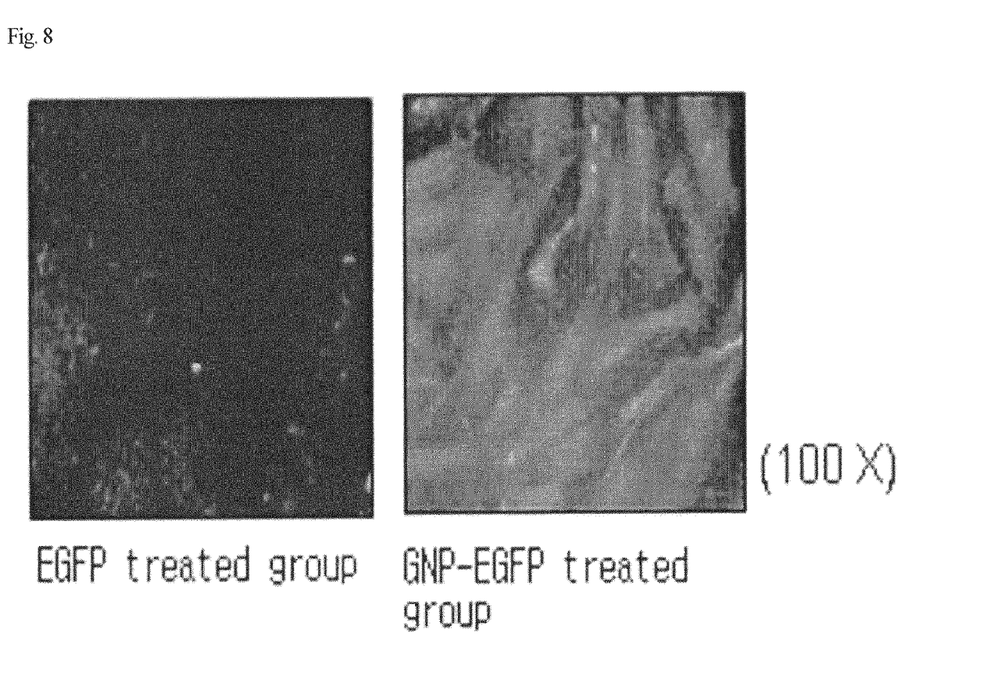
FIG. 8 is photographs that the purified recombinant protein GNP-EGFP was introduced in an animal cell line H9c2, and proteins delivered into cells were analyzed using a fluorescent microscope.

Said target proteins may be easily expressed and mass-produced by incubating said transformed cells in appropriate media, or transducing said transformed cells into an optional animal and then incubating them in vivo. In preferred examples of the present invention, recombinant proteins that EGFPs were fused with transmembrane delivery peptides, were expressed and purified by transducing the recombinant expression vector pGNP-EGFP, wherein EGFP genes were inserted into pGNP vector, into *Escherichia coli* strain BL21 (pLysS), to prepare transformants, and incubating them in appropriate media (ref. FIGS. 4 and 5). According to the preferred examples of the present invention, when said recombinant fusion proteins are treated in animal cell lines, proteins are delivered into cells in much higher rate, compared to a case that natural EGFPs without fused GNP are treated (ref. FIGS. 7 and 8). Therefore, when methods of the present invention are used, the desired substances, for example, proteins, nucleic acids, drugs and the like may be efficiently delivered into animal cells including human, and thus the present invention may be usefully used as uses for delivering drugs, and the like.

MODE FOR INVENTION

The present invention is explained in detail below, with reference with examples.

But, the examples below are intended to illustrate the present invention, wherein the scope of the present invention is not restricted to them.

Example 1

Preparation of Double Strand DNA Coding GNP-TDP Peptide

Figure 1:
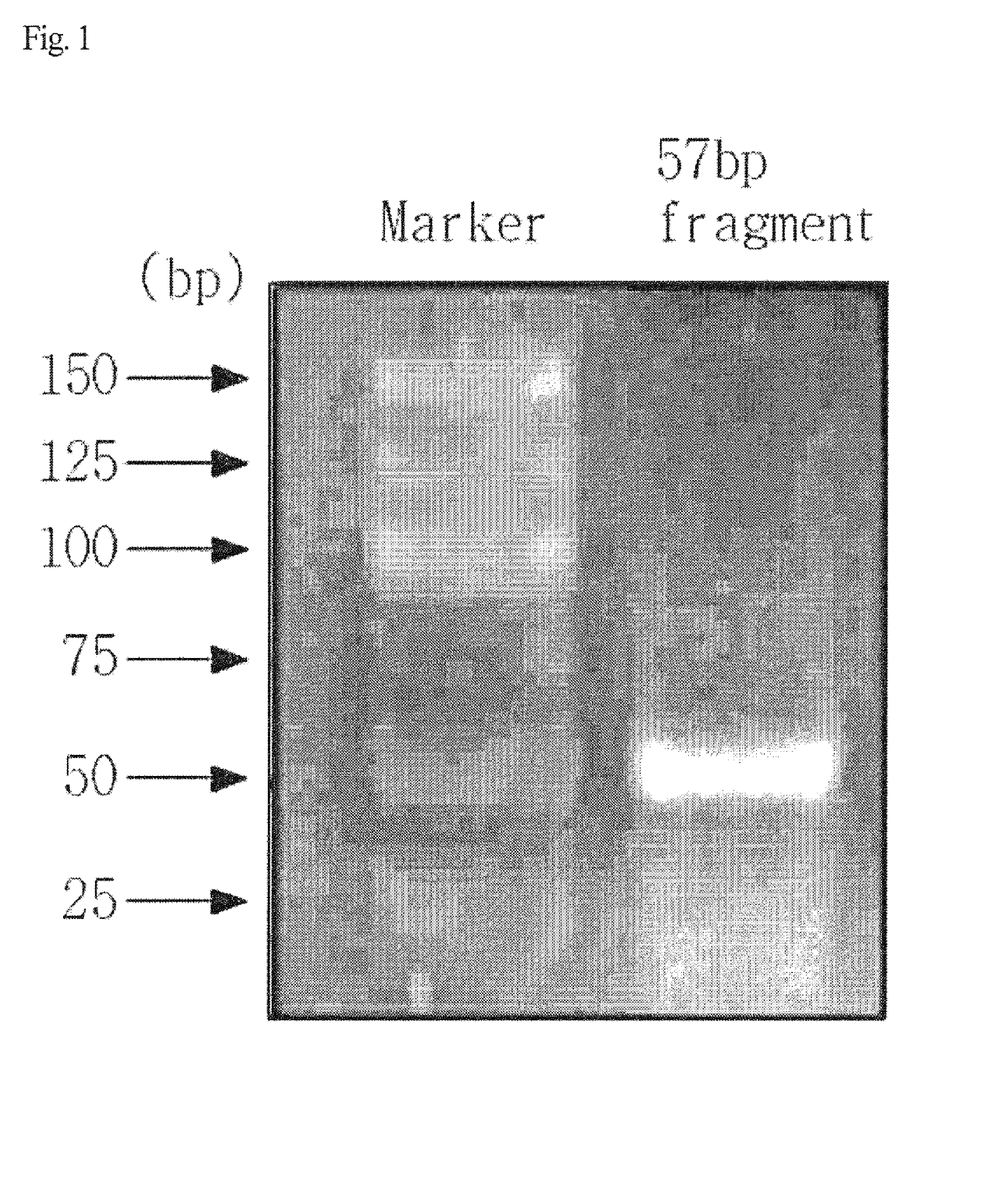
FIG. 1 is an electrophoresis photograph showing a DNA fragment obtained by annealing the complementary DNA sequence with a length of 57 bp comprising a base sequence coding a GNP-TDP peptide, and amplifying the sequence.

A double strand DNA comprising a base sequence coding a GNP-TDP peptide was prepared by coupling one strand oligomer, described in SEQ ID No. 3, comprising a DNA sequence coding an 11 amino acid sequence from $29^{th}$ alanine to $39^{th}$ arginine in a total 381 amino acid sequences of human G protein alpha 12 (GenBank Accession Numbers AAH87537, BC087537) with an oligomer, described in SEQ ID No. 4, with its complementary sequence. Specifically, said DNA oligomer is the sequence of a total 57 bp comprising a DNA sequence, described in SEQ ID No. 2 with 33 bases coding the GNP-TDP and a recognition site of restriction enzymes NdeI and BamHI, and its complementary sequence. Said oligomers were treated at 80° C. for 15 minutes and cooled at room temperature, and double strand DNA of 57 bp was prepared by coupling two oligomers. The resulting product amplified from the reaction was identified in 2% Agarose gel electrophoresis. As a result, the DNA fragment of 57 bp was amplified (FIG. 1).

Example 2

Construction of pGNP Vector

A pGNP, recombinant expressing vector *Escherichia coli* strains, was constructed using the 57 bp DNA fragment prepared in Example 1 above. Specifically, after performing 2% agarose gel electrophoresis to said 57 bp DNA fragment, DNA was isolated using QIAquick PCR purification kit (Qiagen, Germany). The isolated DNA fragment was digested with restriction enzymes NdeI and BamHI, and a pET28a vector (Novagen, USA) also digested with the same restriction enzymes. Then, they were reacted with a T4 DNA ligase (Promega, USA) to prepare novel plasmid vector, which is called "pGNP," that a DNA fragment coding the peptide of the present invention was inserted (FIG. 2).

Said pGNP vector was transformed into *Escherichia coli* XL1-Blue strain. Then, it was incubated in LB (Luria Botani) plate medium with kanamycin (50 μg/ml). The plasmid DNA was isolated from a colony to be formed in the transformed *Escherichia coli* strain, and the DNA base sequence analysis was performed, using a T7 promoter sequence (TAATAC-GACTCACTATAGGG) as a primer and a DNA base sequence analyzer (ABI system, USA). As a result, it was identified that the DNA fragment amplified by the PCR was a DNA sequence of GNP-TDP, described in SEQ ID No. 2.

Example 3

Construction of pGNP-EGFP Plasmid

To directly identify intracellular delivery efficiency of GNP-TDP in the pGNP vector prepared in Example 2 above, EGFP genes selected as a target protein were inserted into the pGNP vector. Said EGFP genes were obtained by performing PCR to pEGFP-N1 (BD Biosciences, USA) vector including full length DNA sequences. As the primers for PCR, a forward primer described in SEQ ID No. 5 and a reverse primer described in SEQ ID No. 6 were used, wherein these primers included recognition sites of restriction enzymes EcoRI and XhoI. The PCR was performed for 35 cycles of the following reaction in PCR reactor: denaturing a template at 95° C. for 1 minute, annealing the template and a primer at 58° C. for 1 minute and extending them at 72° C. for 1 minute. About 720 bp DNA fragment amplified from the reaction was identified in 1% agarose gel electrophoresis, and then was isolated using QIAquick PCR purification kit. The isolated DNA fragment was digested with restriction enzymes EcoRI and XhoI and inserted into the pGNP vector digested with the same restriction enzymes by reacting with the T4 DNA ligase, whereby novel plasmid "pGNP-EGFP" that EGFP genes coding a target protein were inserted, was prepared.

Said pGNP-EGFP vector was transformed into *Escherichia coli* XL1-Blue strain, and incubated in LB plate medium with kanamycin (50 μg/ml) to select a colony to be formed in the transformed *Escherichia coli*. The pGNP-EGFP was isolated from the selected *Escherichia coli* colony, and it was subjected to PCR analysis and DNA base sequence analysis. As a result, it was identified that EGFP genes were included. Said pGNP-EGFP was introduced into *Escherichia coli* strain DH5a to prepare and preserve transformants.

Example 4

Expression and Purification of GNP-EGFP Recombinant Protein in *Escherichia coli*

A fused protein GNP-EGFP was prepared in an *Escherichia coli* strain, using the vector pGNP-EGFP prepared in Example 3 above. The recombinant vector pGNP-EGFP was introduced into *Escherichia coli* strain BL21 (pLysS) for over-expressing proteins, and transformed. Then, the colony which formed in LB plate medium supplemented with antibiotics of kanamycin (50 μg/ml) and chloramphenicol (34 μg/ml), was inoculated in LB liquid medium and incubated at 37° C. for 16 hours to obtain sufficient culture solution, and the solution was inoculated in fresh LB liquid medium. After culturing the medium in shaking incubator at the same temperature, when an optical density at a wavelength of 600 nm was 0.6, IPTG (isopropyl-β-D-thiogalactopyranoside) was added thereto, so that the final concentration was 0.5 mM, for over-expression of proteins, and the medium was further incubated for 4 hours. Culture solutions sampling by the hour were identified in 12% SDS-polyacrylamide gel electrophoresis. As a result, it confirmed that recombinant protein GNP-EGFP was expressed (FIG. 4).

To isolate and purify the recombinant protein GNP-EGFP, the culture solutions were collected in a centrifuge, and were dissolved with the buffer solution (6 M Urea, 500 mM NaCl, 20 mM Tris-HCl, pH 8.0). A procedure of freezing and thawing at −80° C. were 3 times repeated so that cell walls were well broken, and then cells were triturated using an ultrasonic processor VCX-500 (Sonics & Materials, USA) and centrifuged to isolate supernatant. The isolated sample was applied in Ni-NTA column (Qiagen, Germany) and Q-sepharose column (Amersham Bioscience, Sweden) to isolate and purify GNP-EGFP proteins (FIG. 5). Said recombinant proteins were desalted using a PD-10 desalting column (Amersham Biosciences, Sweden), and glycerol was added thereto to be a concentration of 10% and the product was stored at −80° C.

Example 5

Delivery of GNP-EGFP Recombinant Proteins into Animal Cell Lines

The recombinant proteins isolated and purified in Example 4 above were delivered into a rat myoblast H9c2 cell line (ATCC CRL-1446), and the delivery efficiency thereof was identified. H9c2 cells were incubated in DMEM medium (Dulbecco's modified Eagle's medium, Gibco, USA), and dispensed to a 6-well plate (Nalge Nunc, USA) in a cell number of 6×10$^5$. Then, when it was grown to 70% subconfluent state, fresh medium supplemented with 10% FBS was replaced. Here, GNP-EGFP recombinant proteins were treated in cells by the concentration (0 to 2.0 μM) for 2 hours, or in a concentration of 0.5 μM for 2 hours. As a control group, natural EGFP proteins without fused GNP peptide were used. After the predetermined time, cells were washed twice with PBS buffer solution (phosphate-buffered saline) and they were treated with EDTA free-trypsin (Gibco-BRL, USA) for 10 minutes to remove proteins that may be attached to cell surfaces, and again washed with PBS.

Figure 6:
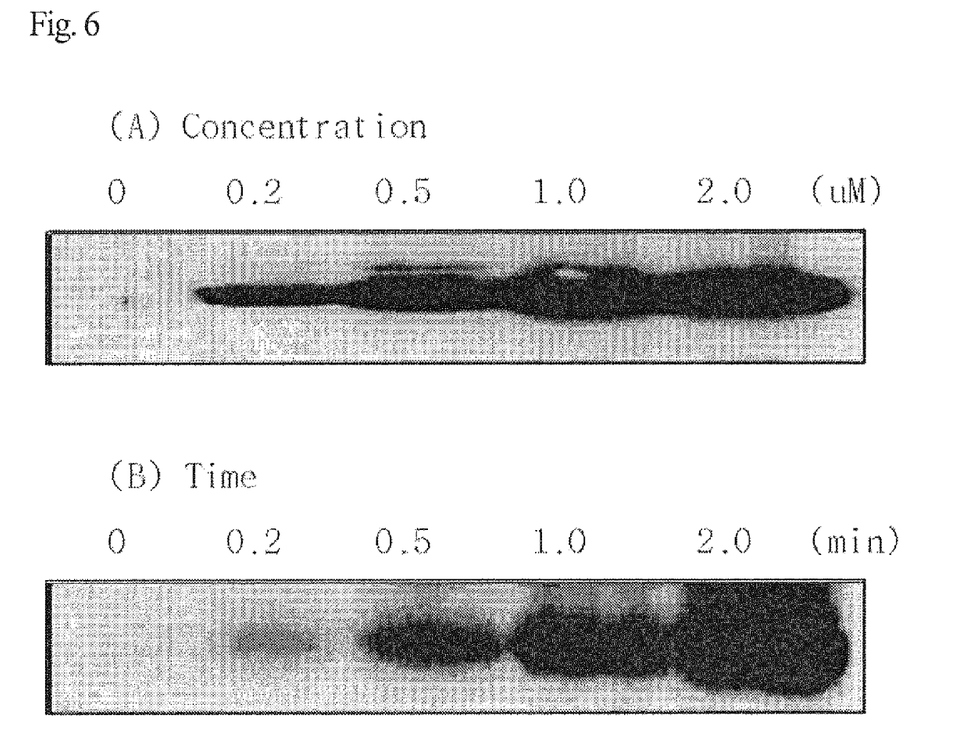
FIG. 6 is electrophoresis photographs showing results that the purified recombinant protein GNP-EGFP was treated in an animal cell line H9c2 by the concentration of protein (A) or by the time (B), and cells were homogenized and analyzed by a Western blot, to identify proteins delivered into cells.

To identify delivery efficiency of the treated recombinant proteins, Western blot analysis, flow cytometry (fluorescence activated cell sorting) and analysis using a fluorescence microscope were performed on said cell lines. First, for Western blot analysis, cells were lysed using lysis buffer solution (20 mM Tris, 150 mM NaCl, 1 mM Na$_2$EDTA, 1 mM EGTA, 1% Triton, 2.5 mM sodium pyrophosphate, 1 mM β-glycerophosphate, 1 mM Na$_3$VO$_4$, 1 mg/ml leupeptin, and 1 mM PMSF), and centrifuged to obtain intracellular whole proteins. 20 μg of proteins were subjected to electrophoresis in 12% SDS-polyacrylamide gel, and proteins included in the electrophoresed gel were absorbed into polyvinylidene fluoride (PVDF) membrane (Gelman, USA). Using an antibody (SantaCruz, USA) against EGFP, Western blot was performed on the membrane by common methods to detect EGFP delivered into cells. As a result, it confirmed that proteins were delivered into animal cell lines, depending on concentrations and times for treating with proteins (FIG. 6).

To verify this result, an experiment was performed using flow cytometry. The animal cell lines H9c2 were dispensed to 6-well plate in a cell number of 2×10$^5$. Then, when cells were grown to 80 to 90% subconfluent state, EGFP or GNP-EGFP recombinant proteins were treated in a concentration of 0.5 μM. After 1 hour, recombinant proteins that could be attached to cell membranes were removed by removing the medium, washing it twice with PBS and treating it with trypsin. Again, it was washed with PBS, and cells were scraped off. Then, 0.5 ml of PBS was added thereto and the mixture was mixed. Then, fluorescence was analyzed using the flow cytometry. As a result, it was identified that EGFP without fused GNP was not delivered into animal cells, whereas GNP-EGFP was efficiently delivered into animal cells (FIG. 7).

Finally, to directly identify proteins substantially delivered into animal cells, an experiment was performed using fluorescence microscope (Olympus BX51, USA). Cells were dispensed to 4-well plate (LAB-TEK II CHAMBER, Nalge Nunc, USA). Then, EGFP or GNP-EGFP recombinant proteins were treated in a concentration of 0.5 μM, followed by treating them with trypsin and washing them with PBS. They were exposed in 3.7% formaldehyde solution at room temperature for 5 minutes, again washed with PBS and mounted to observe via the microscope. As a result, it was identified that recombinant proteins were efficiently delivered into animal cell lines (FIG. 8).

INDUSTRIAL APPLICABILITY

As shown in the above, since transmembrane delivery peptides of the present invention can be efficiently delivered into animal cell lines, they may be usefully used for the purposes of delivering various target materials, including proteins, nucleic acid, drugs and the like.

The invention claimed is:

1. A transmembrane delivery peptide consisting of an amino acid sequence described in SEQ ID No. 1.

2. A nucleic acid coding for the transmembrane delivery peptide of claim 1.

3. The nucleic acid according to claim 2, wherein the nucleic acid consists of a base sequence described in SEQ ID No. 2.

4. A recombinant vector comprising the nucleic acid of claim 2.

5. The recombinant vector according to claim 4, wherein a nucleic acid coding for a target protein is inserted into said recombinant vector in a manner that the target protein is fused with a transmembrane delivery peptide consisting of an amino acid sequence described in SEQ ID No. 1 and expressed as a fusion protein.

6. A transformant cell prepared by introducing the recombinant vector of claim 4 to a cell.

7. A transformant cell prepared by introducing the recombinant vector of claim 5 to a cell.

8. A method for expressing a target protein fused with a transmembrane delivery peptide consisting of the amino acid sequence described in SEQ ID No. 1, characterized by incubating the transformant of claim 6 in a medium, or introducing the transformant into an animal.

9. A method for introducing a target protein into cells, characterized by introducing the recombinant vector of claim 5 into a cell culture or into an animal.

10. A method for expressing a target protein fused with the transmembrane delivery peptide consisting of the amino acid sequence described in SEQ ID No. 1, characterized by incubating the transformant of claim 7 in a medium, or introducing the transformant into an animal.

* * * * *